US 10,742,786 B2

(12) United States Patent
    Goeltner

(10) Patent No.: US 10,742,786 B2
(45) Date of Patent: Aug. 11, 2020

(54) MOBILE DEVICE WITH SIDE-LOOKING BIOMETRIC SENSOR

(71) Applicant: OSRAM Opto Semiconductors GmbH, Regensburg (DE)

(72) Inventor: Christoph Goeltner, Cupertino, CA (US)

(73) Assignee: OSRAM Opto Semiconductors GmbH, Regensburg (DE)

( * ) Notice: Subject to any disclaimer, the term of this patent is extended or adjusted under 35 U.S.C. 154(b) by 0 days.

(21) Appl. No.: 16/192,595

(22) Filed: Nov. 15, 2018

(65) Prior Publication Data

US 2020/0162592 A1    May 21, 2020

(51) Int. Cl.
| | |
|---|---|
| *G06K 9/00* | (2006.01) |
| *H04M 1/02* | (2006.01) |
| *A61B 5/1455* | (2006.01) |
| *A61B 5/00* | (2006.01) |
| *G06F 3/03* | (2006.01) |
| *A61B 5/02* | (2006.01) |

(52) U.S. Cl.
  CPC ............... *H04M 1/026* (2013.01); *A61B 5/02* (2013.01); *A61B 5/14552* (2013.01); *A61B 5/6898* (2013.01); *G06F 3/0304* (2013.01); *A61B 2560/0462* (2013.01); *G06K 9/0004* (2013.01); *H04M 2250/12* (2013.01)

(58) Field of Classification Search
  None
  See application file for complete search history.

(56) References Cited

U.S. PATENT DOCUMENTS

| | | | | |
|---|---|---|---|---|
| 7,439,849 | B2 * | 10/2008 | Kameyama | B60Q 1/50 340/425.5 |
| 9,811,713 | B2 * | 11/2017 | Pi | H04L 63/0861 |
| 10,019,562 | B2 | 7/2018 | Willis et al. | |
| 10,061,959 | B2 * | 8/2018 | Chin | G06K 9/00013 |
| 2003/0115490 | A1 * | 6/2003 | Russo | G06K 9/00026 726/5 |
| 2014/0275850 | A1 | 9/2014 | Venkatraman et al. | |
| 2016/0063230 | A1 * | 3/2016 | Alten | G06F 21/32 726/28 |
| 2016/0128217 | A1 | 5/2016 | Yoo et al. | |
| 2016/0253544 | A1 * | 9/2016 | Weber | G06F 1/1626 382/124 |
| 2019/0026527 | A1 * | 1/2019 | He | G02B 6/0026 |

FOREIGN PATENT DOCUMENTS

EP       1685794 A1    8/2006

* cited by examiner

*Primary Examiner* — Tuan A Tran
(74) *Attorney, Agent, or Firm* — Slater Matsil, LLP

(57) ABSTRACT

A mobile device with a side-looking biometric sensor, a sensor and a method for sensing a biometric function of a user holding a mobile device a disclosed. In an embodiment, a mobile device has a generally flat rectangular shape with a relatively large front and rear surfaces and relatively small upper side, lower side, left side and right side surfaces, wherein the mobile device includes a sensor configured for capturing biometric data of a user holding the mobile device. The sensor includes a light source configured for emitting light towards a hand of the user and a photodetector configured for receiving light emitted from the light source and reflected back from the hand, wherein the sensor is a side-looking sensor.

12 Claims, 6 Drawing Sheets

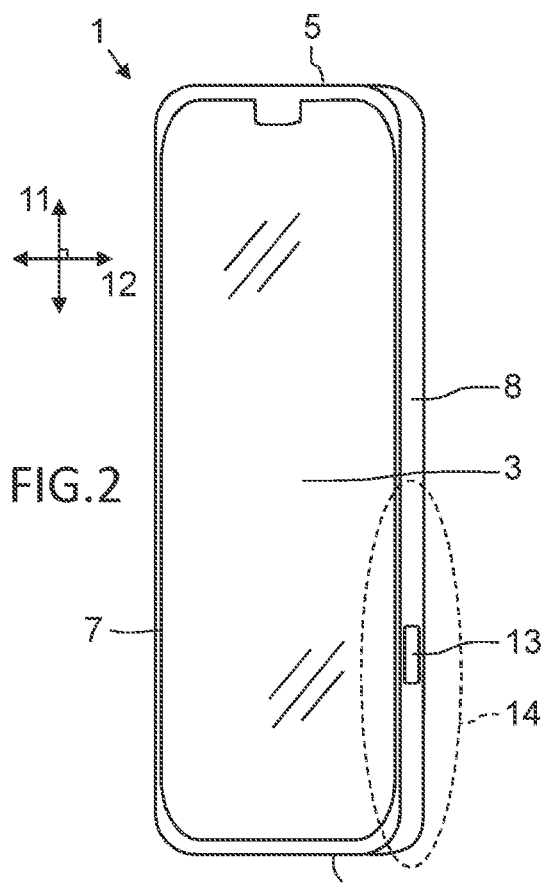
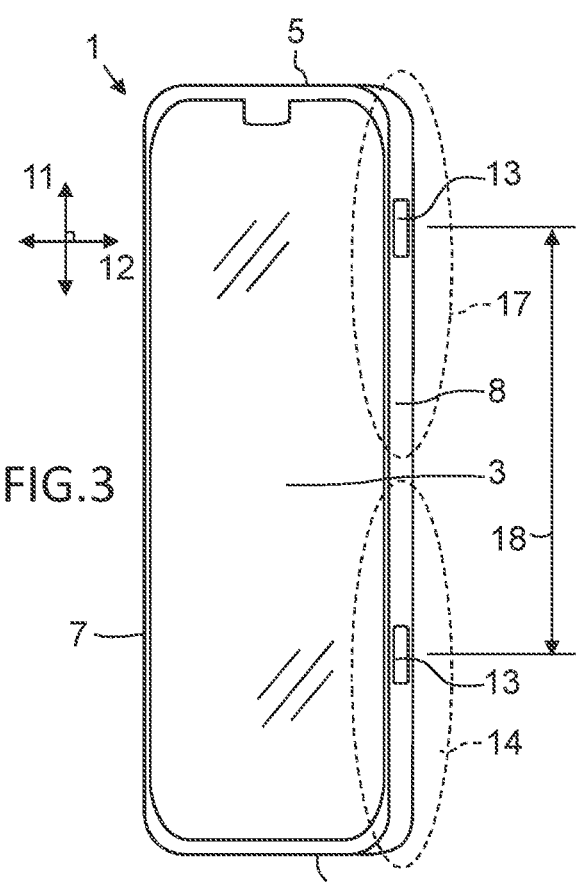
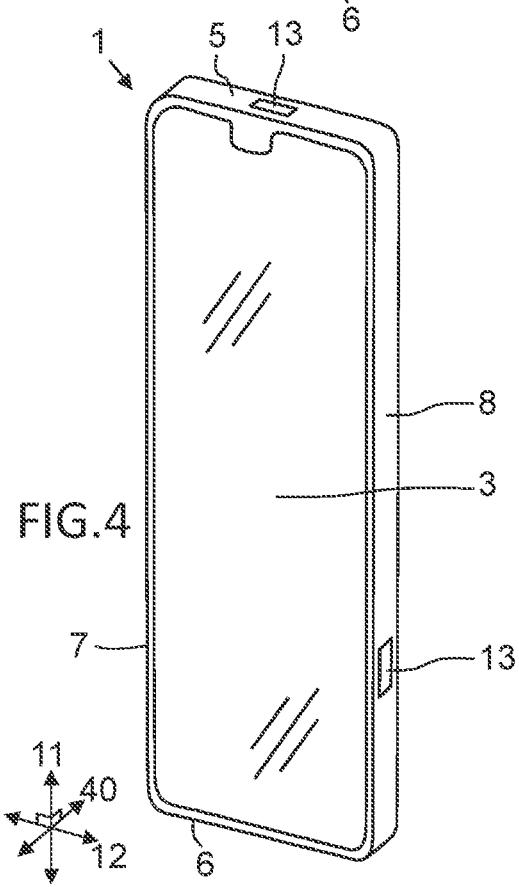
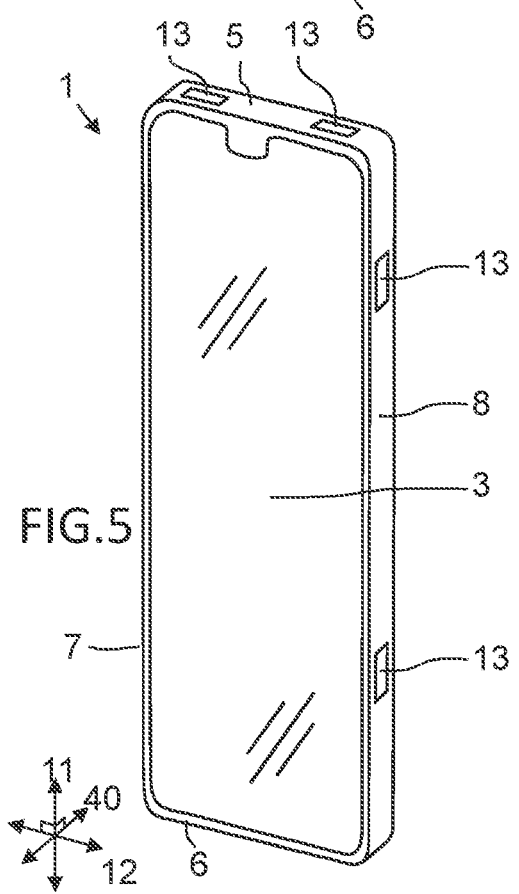

MOBILE DEVICE WITH SIDE-LOOKING BIOMETRIC SENSOR

TECHNICAL FIELD

The disclosure relates to a mobile device comprising a sensor configured for capturing biometric data of a user holding the mobile device. The disclosure also relates to a sensor configured for being installed in a mobile device and capturing biometric data of a user of the mobile device, as well as a method for sensing a biometric function of a user holding a mobile device.

Although the disclosure will be described primarily in relation to a mobile telephone, the disclosure is not restricted to this particular type of mobile device, but may alternatively be implemented in other types of mobile devices, such as notebook computers, tablet computers, laptop computers, portable media players, handheld game controllers or handheld game consoles.

BACKGROUND

Mobile devices comprising a sensor configured for capturing biometric data of a user holding the mobile device may be used for simple and quick detection of a variety of biometric functions of a user, such as heart rate and blood oxygen content.

In the field of mobile devices with biometric sensor, in particular those mobile devices having an electronic display on a front surface of the device, there is an increasing demand for increasing the size of the display while keeping the mobile device relatively small and portable for easy handling and/or bringing along. There is also a need for further simplified sensing of a biometric function of a user holding the mobile device.

Despite the activities in the field, there is still a demand for an improved mobile device, which is capable of meeting the requirements as to display size, compactness, handling and simplified sensing.

SUMMARY OF THE DISCLOSURE

This section provides a general summary of the disclosure, and is not a comprehensive disclosure of its full scope or all of its features.

Embodiments provide a mobile device with biometric sensor, a method for sensing a biometric function and a sensor configured for being installed in a mobile device and capturing biometric data, which enables simplified sensing of a biometric function of a user holding the mobile device. Further embodiments enable an increased display size while keeping the mobile device relatively small and portable for easy handling and/or bringing along.

According to a first aspect of the present disclosure, a mobile device is provided, wherein the mobile device has a generally flat rectangular shape with a relatively large front and rear surfaces and relatively small upper side, lower side, left side and right side surfaces, wherein the mobile device comprises a sensor configured for capturing biometric data of a user holding the mobile device, the sensor comprising a light source configured for emitting light towards a hand of the user and a photodetector configured for receiving light emitted from the light source and reflected back from the hand, wherein the sensor is a side-looking sensor.

According to a second aspect of the present disclosure, a sensor is provided, wherein the sensor is configured for being installed in a mobile device and capturing biometric data of a user of the mobile device, the sensor comprising a light source configured for emitting light towards a hand of the user, a photodetector configured for receiving light emitted from the light source and reflected back from the hand, and an electrical connector for communication with a central processing unit of the mobile device, wherein a facing direction of the electrical connector is perpendicular to a facing direction of a photosensitive area of the photodetector.

According to a third aspect of the present disclosure, a method for sensing a biometric function of a user holding a mobile device is provided, wherein the mobile device has a generally flat rectangular shape with a relatively large front and rear surfaces and relatively small upper side, lower side, left side and right side surfaces. The method comprises the steps of emitting light from a light source towards a hand of the user, and receiving by means of a photodetector light emitted from the light source and reflected back from the hand, wherein the sensor is a side-looking sensor.

According to an embodiment, by having the sensor configured as a side-looking sensor, the sensor does not require any space of the front surface of the mobile device. Consequently, the side-looking arrangement of the sensor enables increased display size with maintained outer dimensions of the mobile device merely by reducing Bezel size, i.e., the outside frame surrounding the display of the mobile device.

According to another embodiment, the side-looking sensor also enables simplified sensing of a biometric function of a user holding the mobile device because a user often tend to hold the mobile device along the sides of the mobile device, i.e., along the edges of the device. This means that a side-looking sensor often automatically will face the hand of the user upon handling and holding of the mobile device, thereby eliminating the need for the user to place the hand or finger on a special location on the front or rear surface of the mobile device.

In addition, a side-looking sensor is less visible to a user and enables thereby a more pleasant and esthetical overall design of the mobile device.

Further features of, and advantages with, the present disclosure will become apparent when studying the appended claims and the following description. The skilled person realize that different features of the present disclosure may be combined to create embodiments other than those described in the following, without departing from the scope of the present disclosure.

BRIEF DESCRIPTION OF THE DRAWINGS

FIGS. 2 and 3 show perspective views of two example embodiments of the mobile device.

FIGS. 4 and 5 show perspective views of two further example embodiments of the mobile device.

DETAILED DESCRIPTION OF ILLUSTRATIVE EMBODIMENTS

Figure 1:
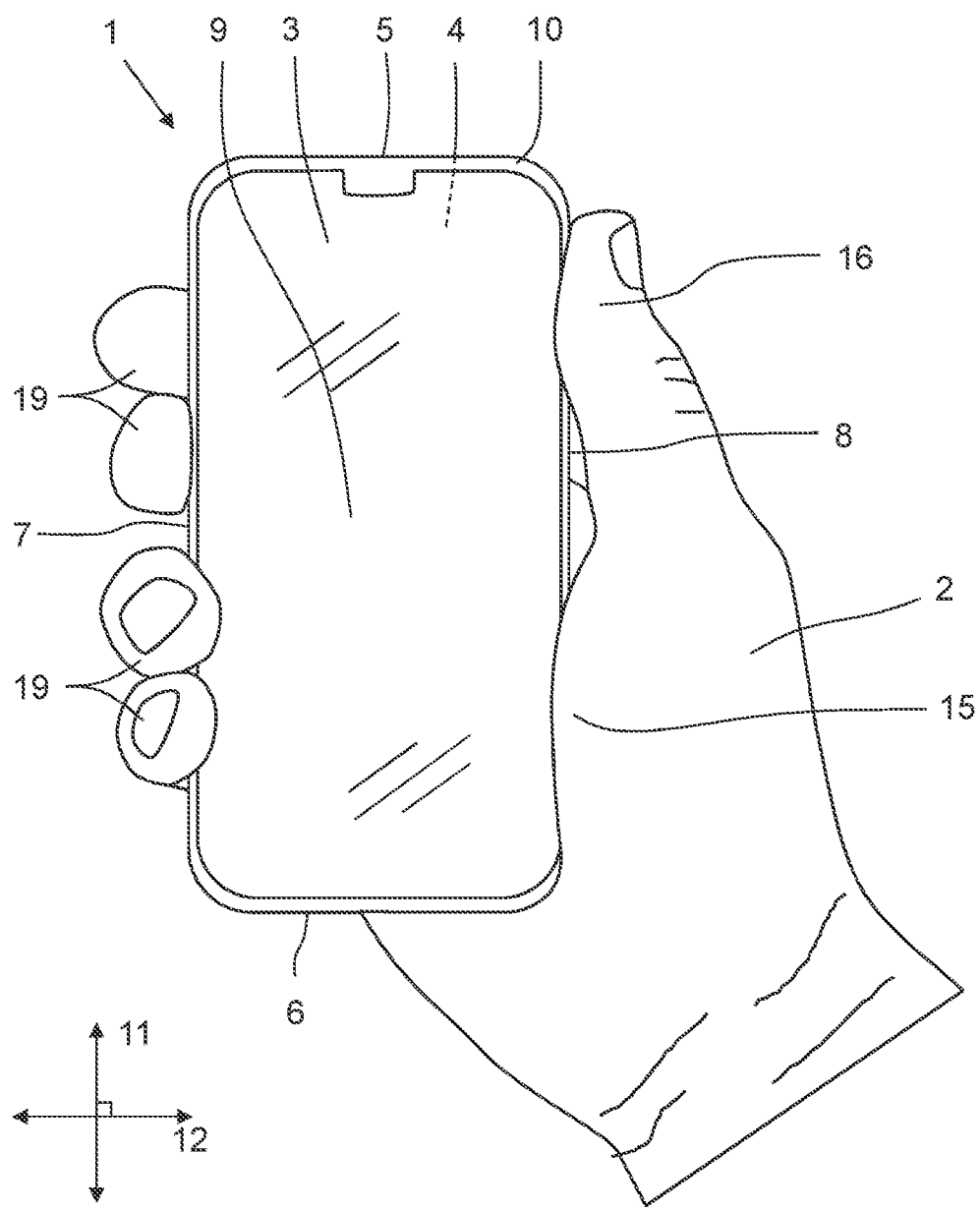
FIG. 1 show a schematic illustration of a front view of an example embodiment of a mobile device held by a hand of a user.

The present disclosure will now be described more fully hereinafter with reference to the accompanying drawings, in which exemplary embodiments of the disclosure are shown. The disclosure may, however, be embodied in many different forms and should not be construed as limited to the embodiments set forth herein; rather, these embodiments are provided for thoroughness and completeness. Like reference characters refer to like elements throughout the description. The drawings are not necessarily to scale and certain features may be exaggerated in order to better illustrate and explain the exemplary embodiments of the present disclosure.

Referring now to FIG. 1, there is shown a schematic illustration of a front view of an example embodiment of a mobile device 1 held by a hand 2 of a user. In this example embodiment the mobile device is illustrated as a mobile cellular telephone, but the disclosure applies equally to other types of mobile devices, such as, for example, notebook computers, tablet computers, laptop computers, portable media players, handheld game controllers or handheld game consoles, or the like.

The mobile device 1 has a generally flat rectangular shape with a relatively large front surface 3 and rear surface 4. The mobile device 1 further has a relatively small upper side surface 5, lower side surface 6, left side surface 7 and right side surface 8. The mobile device 1 also has an electronic display 9 arranged on the front surface 3 and surrounded by a bezel 10.

In FIG. 1, the mobile device 1 has left and right side surfaces 7, 8 that are longer than the upper and lower side surfaces 5, 6. Consequently, the mobile device has a rectangular shape with a larger extension in a longitudinal direction 11 of the mobile device than a transverse direction 12. The thickness of the mobile device 1 generally much smaller than the extension in the longitudinal or transverse direction 11, 12 of the mobile device 1.

As schematically illustrated in the example embodiment of FIG. 2, the mobile device 1 may comprise a sensor 13 configured for capturing biometric data of the user holding the mobile device 1. This may, for example, be performed by having an optoelectronic sensor 13 comprising a light source configured for emitting light towards a hand 2 of the user and a photodetector configured for receiving light emitted from the light source and reflected back from the hand 2. As described more in detail below, the various biometric data of the user may be detected and captured by analyzing the properties of the reflected light.

Importantly, the sensor 13 is a side-looking sensor. This means that the sensor is arranged to operate in a facing direction of any of the upper side surface 5, lower side surface 6, left side surface 7 and right side surface 8.

In other words, the sensor 13 is configured to emit light in an emitting direction that is substantially parallel with a plane of the front surface 3, i.e., substantially perpendicular to a facing direction of the front surface 3 of the mobile device, and the photodetector is configured for receiving reflected light in a receiving direction that also is substantially parallel with a plane of the front surface 3, i.e., substantially perpendicular to said facing direction of the front surface 3 of the mobile device. The emitting and receiving direction may of course vary a certain degree from a direction that is exactly perpendicular to said facing direction, e.g., about +/−45 degrees, specifically about +/−20 degrees from an exact perpendicular direction to said facing direction.

With respect to the photodetector, this means that a facing direction of a photosensitive area of the photodetector is oriented substantially perpendicular to the facing direction of the front surface 3.

By arranging one or more sensors 13 as side-looking sensors on the mobile device 1 a user viewing the front or rear surfaces 3, 4 of the mobile device 1 will typically not see any part of the one or more sensors 13. The side-looking arrangement of the sensors 13 thus also contributes to a more overall esthetical impression of the mobile device 1.

In the example embodiment of FIG. 2, the mobile device 1 comprises a side-looking sensor 13 located on a lower region 14 of the right side surface 8 of the mobile device 1, as seen with the mobile device 1 oriented in a vertical plane with the upper side surface 5 facing upwards. This position of the sensor 11 enables simplified detection of biometric data of the user because the palm 15 of the right hand of a user, in particular the group of muscles on the palm of the right hand at the base of the thumb 16, will often automatically come into contact with the sensor 13 as soon as the user holds the mobile device 1 in the right hand 2. This is, for example, illustrated in FIG. 1.

In other words, the mobile device 1 and/or any software applications running on the mobile device 1 can be configured for automatic detection and monitoring of various biometrical data of the user, for example, for the purpose of providing accurate and reliable reports of current and historical health status of the user, all without the user having to hold the mobile device 1 in a unnatural position or press the finger on a sensor on the rear surface 4 of the mobile device 1.

Although not illustrated in FIG. 2, the mobile device 1 may according to a further example embodiment of the mobile device comprise at least one side-looking sensor 13 configured for capturing biometric data on each of the left and right side surfaces 7, 8. Hence, the mobile device 1 of FIG. 2 may, for example, in addition to the sensor 13 located on the right side surface 8, further comprise an additional sensor 13 configured for capturing biometric data located on the left side surface 7 of the mobile device 1. Thereby, accurate and reliable detection and sensing of biometrical data of the user may be acquired for both right-handed and left-handed users. Specifically, both the sensor and additional sensor are located on a lower region 14 of the right side surface and left side surface of the mobile device 1, respectively.

FIG. 3 schematically illustrates a further example embodiment of the mobile device 1, wherein the mobile device comprises two side-looking sensors 13 configured for capturing biometric data on two individual and spaced apart locations on the right side surface 8 of the mobile device 1. For example, the mobile device 1 may comprise a side-looking sensor 13 located on a lower region 14 of the right side surface 8 of the mobile device 1, and an additional side-looking sensor 13 located on an upper region 17 of the right side surface 8 of the mobile device 1, as seen with the mobile device 1 oriented in a vertical plane with the upper side surface 5 facing upwards.

The location of the additional side-looking sensor 13 on the upper region 17 of the right side surface 8 may, for example, be selected such as to come in contact with a thumb 16 of a hand of a user upon conventional holding of the mobile device 2, as for example, is illustrated in FIG. 1.

Two side-looking sensors arranged spaced apart on the same side surface, such as the right side surface 8 as illustrated in FIG. 3, provides several advantages. For example, the likelihood that the hand 2 of the user covers at least one of the two side-looking sensors 13 is increased, compared with a single side-looking sensor 13 on the side surface, thereby increasing the likelihood of successful detection and monitoring of biometric data upon use of the mobile device 1.

In fact, for even further increasing the likelihood a successful detection and monitoring of biometric data of the user the mobile device may include at least three, and more specifically at least four side-looking sensors 13 configured for capturing biometric data on individual and spaced apart locations on the right side surface 8 of the mobile device 1.

Moreover, having two side-looking sensors arranged spaced apart from each other enables detection and monitoring of other types of biometric functions, such as, for example, blood pulse wave velocity (PWM). PWM may be, for example, be determined by measuring blood pressure waveforms at each sensor simultaneously. The measured blood pressure waveforms are subsequently analyzed for determining the delay time between them, and with information about a predetermined distance 18 between the two sensors 13 the PWV at the hand of the user may be calculated.

The blood PWV as such is a relevant biometric function for monitoring human health conditions, and there is a certain level of correlation between the blood PWV and blood pressure, thereby enabling the mobile device to perform sensing of additional biometric data, as well as providing accurate estimates of the actual blood pressure of the user.

Although not illustrated in FIG. 3, the mobile device 1 may according to a further example embodiment of the mobile device comprise at least two side-looking sensors 13 configured for capturing biometric data on each of the left and right side surfaces 7, 8. Hence, the mobile device 1 of FIG. 3 may, for example, include two individual and side-looking sensors located also on the left side surface 7 of the mobile device 1, in addition the two individual and spaced apart sensors 13 on the right side surface 8. Thereby, accurate and reliable detection and sensing of biometrical data of the user may be acquired irrespective of with which hand the user is holding the mobile device, e.g., for both right-handed and left-handed users. The locations of the two side-looking sensors in the longitudinal direction 11 on the left side surface 7 of the mobile device 1 may then be identical with the locations in the longitudinal direction 11 of the sensors 13 on the right side surface 8 of the mobile device 1.

Alternatively, the two individual and side-looking sensors located on the left side surface 7 of the mobile device 1, in addition the two individual and spaced apart sensors 13 on the right side surface 8, may be provided for enabling detection of biometric data of one or more of the fingers 19 of the user, as illustrated in FIG. 1. FIG. 1 shows that conventional holding of the mobile device 1 involves clamping the left and right side surfaces 7, 8 of the mobile device 1 between the palm 15 and the fingers 19. Detection and sensing of biometrical data of both the palm 15 and the fingers 19 may offer increased detection of various biometric functions of the user. The locations of the two side-looking sensors in the longitudinal direction 11 on the left side surface 7 of the mobile device 1 may then be selected to match the estimated position of one or more fingers 19, and may thus be different from the locations in the longitudinal direction 11 of the sensors 13 on the right side surface 8 of the mobile device 1.

According to some example embodiments of the mobile device 1, the mobile device 1 may comprise at least two, or at least three, or even at least four side-looking sensors 13 configured for capturing biometric data on each of the left and right side surfaces 7, 8. Thereby, increased likelihood of detection of biometric data of the user is provided and detection of a larger variety of biometric functions is made possible.

FIG. 4 shows still an alternative example embodiment of the mobile device 1 according to the disclosure. Here, the mobile device 1 comprises one side-looking sensor 13 configured for capturing biometric data on each side surface 5, 6, 7, 8 of the mobile device 1, although only the sensors 13 on the right side surface 8 and upper side surface 5 are visible in FIG. 4.

In other words, the mobile device 1 comprises at least one side-looking sensor 13 configured for capturing biometric data on each of the upper side surface 5, lower side surface 6, left side surface 7 and right side surface 8 of the mobile device 1. This arrangement may be particularly beneficial for being able to provide increased possibilities of detecting and capturing biometric data of the user also when the user is holding the mobile device 1 in a landscape orientation, in particular with two hands. Holding the mobile device 1 in a landscape orientation means holding the mobile device 1 arranged with its longitudinal direction 11 substantially aligned with a horizontal direction.

Holding the mobile device 1 in a landscape orientation is, for example, often performed when playing games on the mobile device 1, and the sensors 13, such as, for example, the sensors 13 arranged on the upper and lower side surfaces 5, 6, may then be located in proper contact with the left and right hand palm of the user, thereby enabling detection of biometric data that may be used as input data for the game, for example, as game control input. For example, the sensors 13 may detect the contact pressure of each of the left and right side hand on the mobile device 1 and use this as control input for the game or other software application.

FIG. 5 shows still an alternative example embodiment of the mobile device 1 according to the disclosure, in which the mobile device 1 comprises two side-looking sensors 13 configured for capturing biometric data on each side surface 5, 6, 7, 8, i.e., on each of the upper side surface 5, lower side surface 6, left side surface 7 and right side surface 8 of the mobile device 1, although only the sensors 13 on the right side surface 8 and upper side surface 5 are visible in FIG. 5. This embodiment of the mobile device 1 has similar benefits as those described with reference to FIG. 4, but with even further increased likelihood of obtaining proper detection of biometric data of the user due to the increased likelihood that a palm 15 or finger 19 of the user will come in detection range of the sensors 13. Moreover, the increased number of sensors 13 enables detection of increased biometric functions.

According to some example embodiments of the mobile device 1, the mobile device 1 may even comprises at least three, or at least four side-looking sensors configured for capturing biometric data on each side surface 5, 6, 7, 8 of the mobile device 1. Thereby, increased likelihood of detection of biometric data of the user is provided, and detection of a larger variety of biometric functions is made possible.

According to still some example embodiments of the mobile device 1, the mobile device 1 may have different number of sensors on the left and right side surfaces 7, 8 compared with the number of sensors 13 of the upper and lower side surfaces 5, 6. This arrangement may, for example, be appropriate when the left and right side surfaces 7, 8 are significantly longer than the upper and lower side surfaces 5, 6. Consequently, the mobile device 1 may comprise at least two, specifically at least three, and more specifically at least four side-looking sensors 13 configured for capturing biometric data on each of the left and right side surfaces 7, 8, and the mobile device may additionally comprise at least two, specifically at least three, and more specifically at least four side-looking sensors 13 configured for capturing biometric data on each of the upper and lower side surfaces 5, 6.

FIGS. 4 and 5 shows an example illustration of the thickness of the relatively flat mobile device 1 in a thickness direction 40 of the mobile device 1. The extension of the mobile device 1 in the thickness direction 40 is generally much smaller than the extension of the mobile device 1 in the longitudinal or transverse direction 11, 12.

Figure 6:
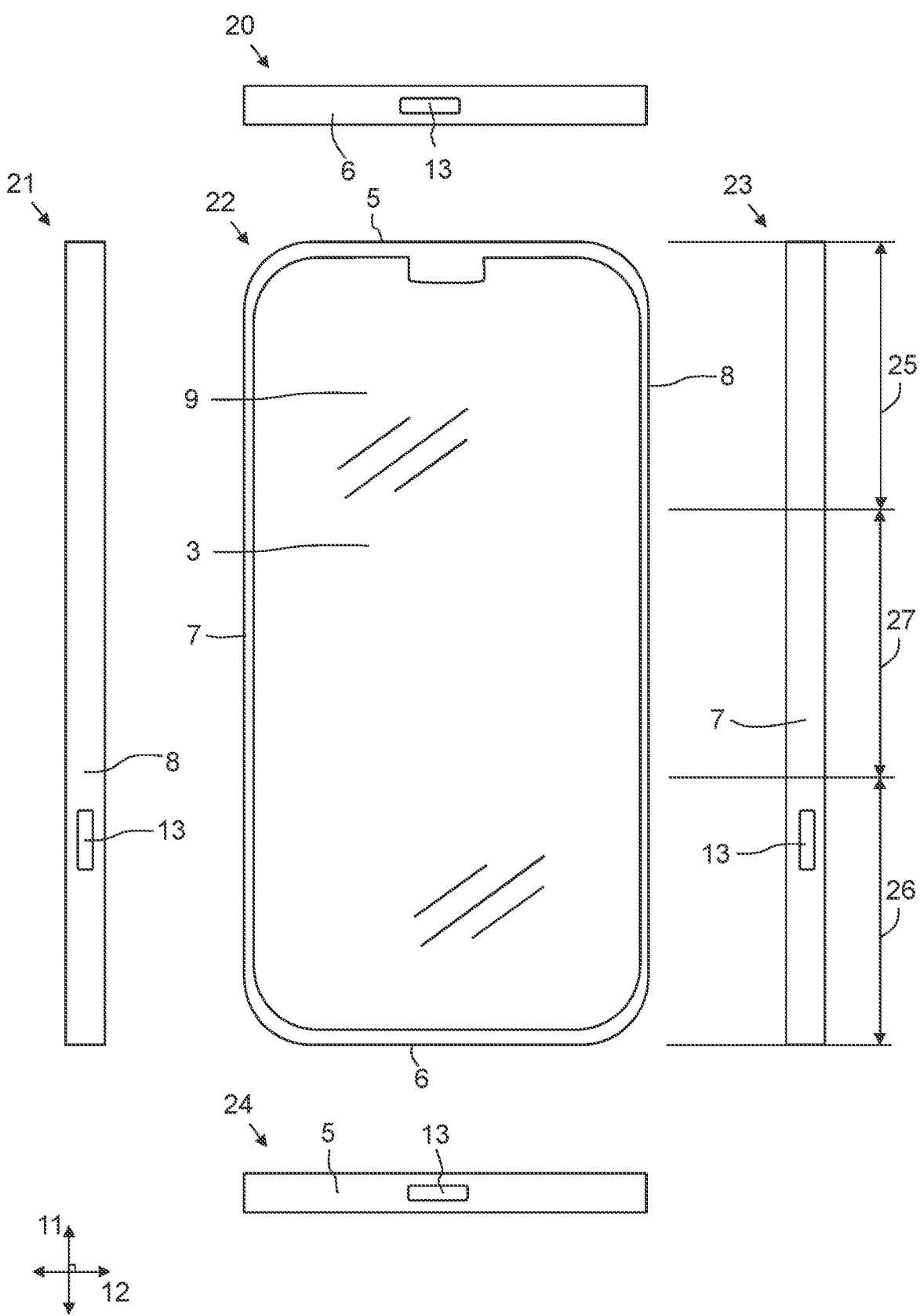
FIGS. 6 and 7 show multiview drawings of two example embodiments of the mobile device.

FIG. 6 shows a multiview illustration of an example embodiment of the mobile device 1 as described with reference to FIG. 4, i.e., a mobile device 1 having one side-looking sensor 13 configured for capturing biometric data on each side surface 5, 6, 7, 8 of the mobile device 1. The multiview illustration, which includes multiple orthographic two-dimensional views of the mobile device 1, comprises a lower side surface view 20, a right side surface view 21, a front surface view 22, a left side surface view 23, and an upper side surface view 24.

As illustrated in the left side surface view 23 of FIG. 6, the mobile device 1 may be divided into three equally long sections, as seen in the longitudinal direction 11, which sections consist of an upper third 25 section, a lower third 26 section and an intermediate third 27 section, as seen with the mobile device oriented in a vertical plane with the upper side surface 5 facing upwards. Moreover, as also illustrated in FIG. 6, the side-looking sensor 13 on each of the left and right side surfaces 7, 8 may be located in the lower third 26 of the mobile device 1. This location of the side-looking sensor 13 on each of the left and right side surfaces 7, 8 may be beneficial for enabling high likelihood of detection of biometric data of the user by means of said sensors 13, because the sensors 13 in the lower third 26 are deemed to match the position of the palm 15 of the user, as shown in FIG. 1.

As also illustrated in FIG. 6, the side-looking sensor 13 on each of the upper and lower side surfaces 5, 6 may be located in a central area of each respective surface, as seen in the transverse direction 12 with the mobile device oriented in a vertical plane with the upper side surface 5 facing upwards. This location of the side-looking sensor 13 on each of the upper and lower side surfaces 5, 6 may be beneficial for enabling high likelihood of detection of biometric data of the user by means of said sensors 13.

Figure 7:
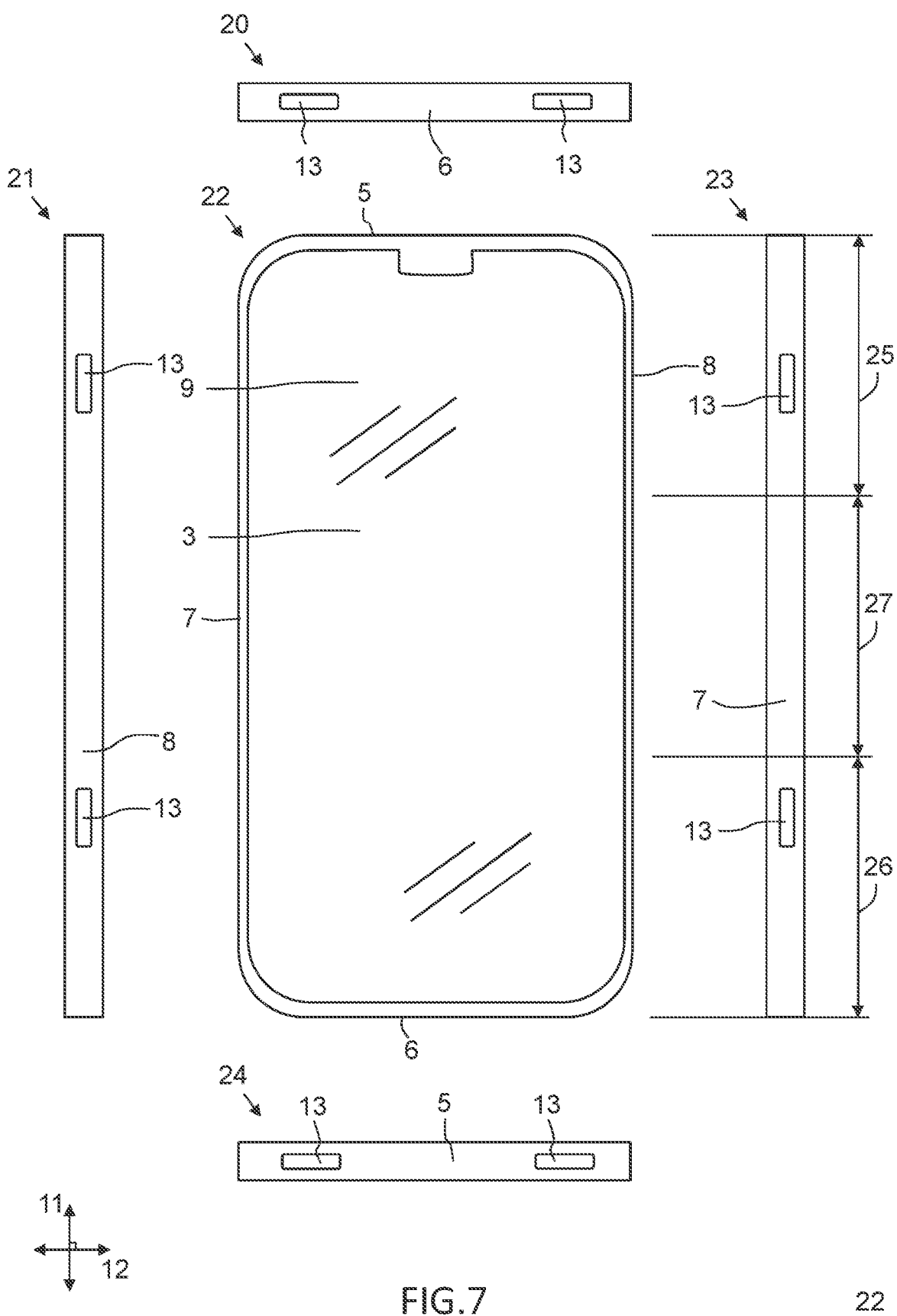

FIG. 7 shows a multiview illustration of an example embodiment of the mobile device 1 as described with reference to FIG. 5, i.e., a mobile device 1 having two side-looking sensors 13 configured for capturing biometric data on each side surface 5, 6, 7, 8 of the mobile device 1. One of the two side-looking sensors 13 on each of the left and right side surfaces 7, 8 may be located in the lower third 26 of the mobile device 1, and the other of the two side-looking sensors 13 on each of the left and right side surfaces 7, 8 may be located in the upper third 25 of the mobile device 1. This arrangement of the two side-looking sensors 13 on each of the left and right side surfaces 7, 8 may be beneficial for enabling high likelihood of detection of biometric data of the user by means of said sensors 13, and being deemed particularly suitable for having the sensors 13 in the lower third 26 matching the position of the palm 15 of the user, and having the sensors 13 in the upper third 25 matching the position of the thumb 16 of the user, as shown in FIG. 1.

As also illustrated in FIG. 7, the two side-looking sensors 13 on each of the upper and lower side surfaces 5, 6 may be located spaced apart and substantially symmetric around a center of the each respective surface, as seen in the transverse direction 12 with the mobile device oriented in a vertical plane with the upper side surface 5 facing upwards. This arrangement of the side-looking sensors 13 on each of the upper and lower side surfaces 5, 6 may be beneficial for enabling high likelihood of detection of biometric data of the user by means of said sensors 13.

Figure 8:
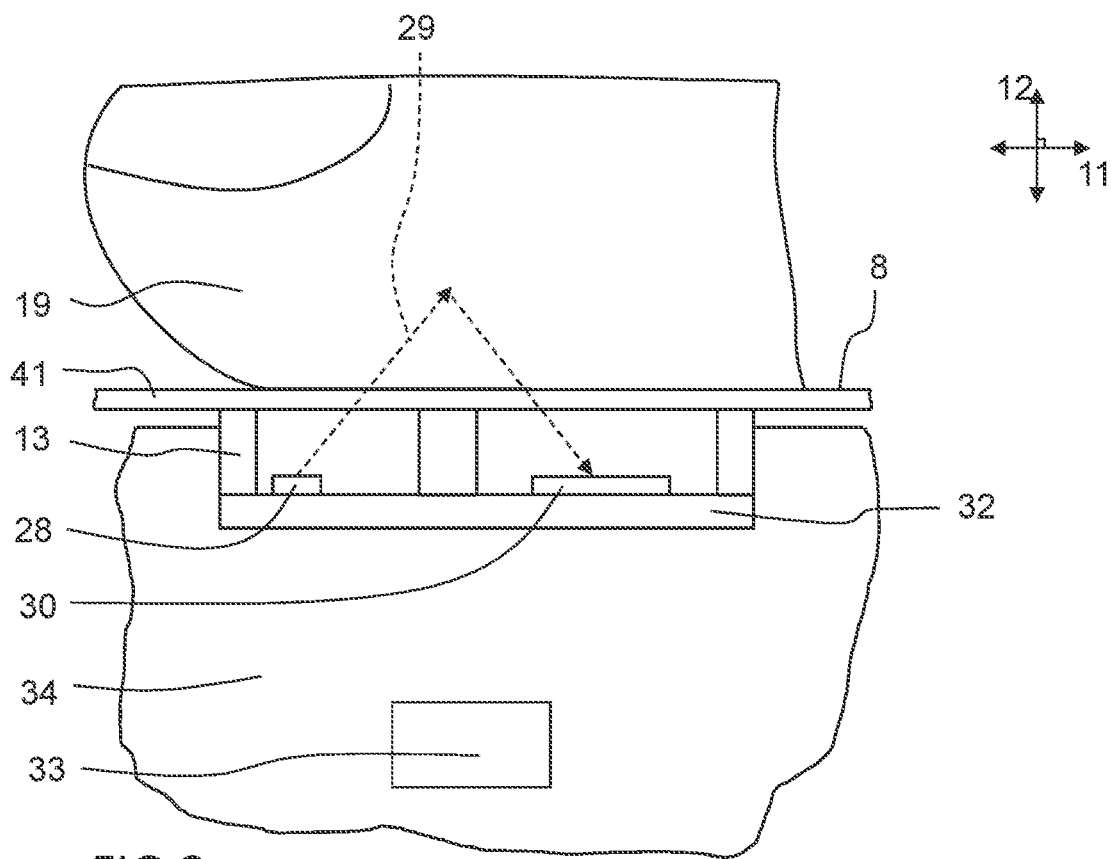
FIG. 8 schematically shows a cross-section of an example embodiment of a sensor.

FIG. 8 schematically shows a cross-sectional view of an example embodiment of a sensor 13 configured for capturing biometric data of a user holding the mobile device 1. The sensor 13 is configured for being installed in a mobile device 1 and comprises a light source 28 configured for emitting light 29 towards a hand 2 or finger 19 of the user and a photodetector 30 configured for receiving light 31 emitted from the light source 28 and reflected back from the hand 2 or finger 19. The sensor 13 may, for example, comprise a planar substrate 32 on which both the light source 28 and photodetector 30 are placed. In the example embodiment of FIG. 8, the sensor 13 is depicted as being installed on the right side surface 8 of the mobile device 2, wherein the light source 28 and photodetector 30 are oriented to detect biometric data sideways, i.e., in the transverse direction 12 of the mobile device.

A cover 41 made of a material that is transmissive to emitted and reflected light and electromagnetic radiation is provided outside of the light source 28 and photodetector 30 for protection of the sensor. The cover 41 may, for example, be made of glass.

The sensor is arranged for being communicatively connected to a central processing unit 33 of the mobile device 1. The central processing unit 33 is typically fastened in a printed circuit board (PCB) 34 and the sensor has to be electrically connected to the PCB as well. The PCB 34 of the main processing unit 33 of the mobile device 1 is generally oriented in a plane that is parallel with a plane of the generally flat mobile device 1, e.g., parallel with a plane of the front surface 3 of the mobile device 1. Consequently, for enabling simple, compact and cost-efficient mounting and connection of the sensor 13 with the central processing unit 33, an electrical connector of the sensor for communication with the central processing unit 33 of the mobile device is arranged such that a facing direction of the electrical connector is perpendicular to a facing direction of a photosensitive area of the photodetector 30.

Figure 9:
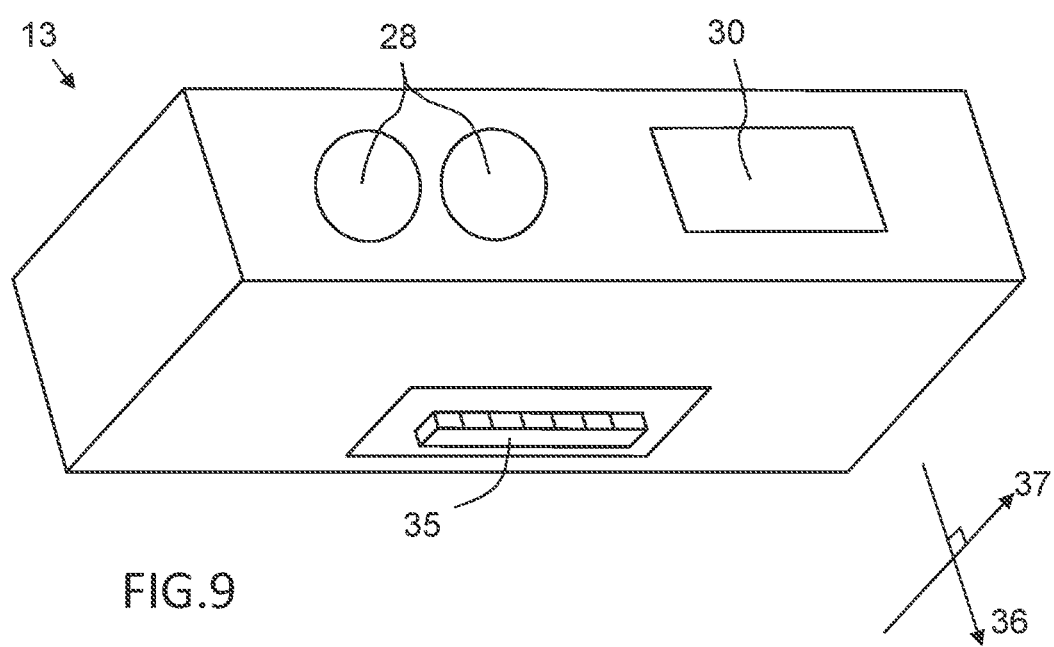
FIG. 9 schematically shows a perspective view of an example embodiment of a sensor.

In other words, when placing the sensor 13 on the mobile device 1 for enabling side-looking operation of the sensor 13, the electrical connector of the sensor 13 is preferably oriented perpendicular to the orientation of the sensing surface of the photodetector 30. This layout of the sensor 13 is schematically illustrated in FIG. 9, which shows an example embodiment of a sensor having two light sources 28, one photodetector 30 and a an electrical connector 35 for connection with a PCB of the mobile device 1. In FIG. 9, the facing direction 36 of the electrical connector is perpendicular to the facing direction 37 of the photosensitive area of the photodetector 30.

The electrical connector 35 may have any conventional form for fastening electrical components to PCB.

The light source 28 is configured to generate visible or invisible light, i.e., electromagnetic radiation, and emit it in a predefined emission direction and/or in a predefined emission angle range. The light source 28 may be configured, for example, as a light-emitting diode or as a laser diode. By way of example, the radiation output by the light source 28 may, for example, constitute green light or red light or any other type of light. Depending on the example chosen, the light may also comprise other wavelengths.

The photodetector 30, or electromagnetic radiation receiver, is configured to receive reflected light (electromagnetic radiation) in a predefined receiving direction and/or in a predefined receiving angle range. The photodetector 30 is configured, for example, as a photodiode that converts incident light into an electrical signal. The sensor 13 may comprises an evaluation unit that is electrically connected to the photodetector 30 and arranged for evaluating the electrical signal.

A basic principle of the sensor 13 consists of the electromagnetic radiation 13 of the light source 28 being emitted in the direction of a measurement object, for example, a palm 15, a thumb 16 or a finger 19. The electromagnetic radiation penetrates into the skin of the user and is scattered and (partly) absorbed by body cells. In this case, the optical properties (scattering/absorption) of blood differ from those of the surrounding body cells. The returned light is, for example, modulated by volumetric expansion of the artery during the heartbeat, such that, for example, heart rate can be detected on the basis of the detected modulation.

The wavelength of the light emitted from the light source 28 may be adapted to match the desired biometrical function, such as heart rate, pulse wave velocity, contact pressure, blood oxygen content, etc. Multiple light sources 28 having the same wavelength or different wavelengths may be used. If the wavelengths of the multiple light sources 28 are similar, the light sources 28 have a redundancy for improved reliability. If the wavelengths of the light sources 28 are different, different types of biometric functions may be measured by means of each individual light source 28. Multiple photodetectors 30 may also be used, each being specifically adapted to detect individual wavelengths.

Figure 10:
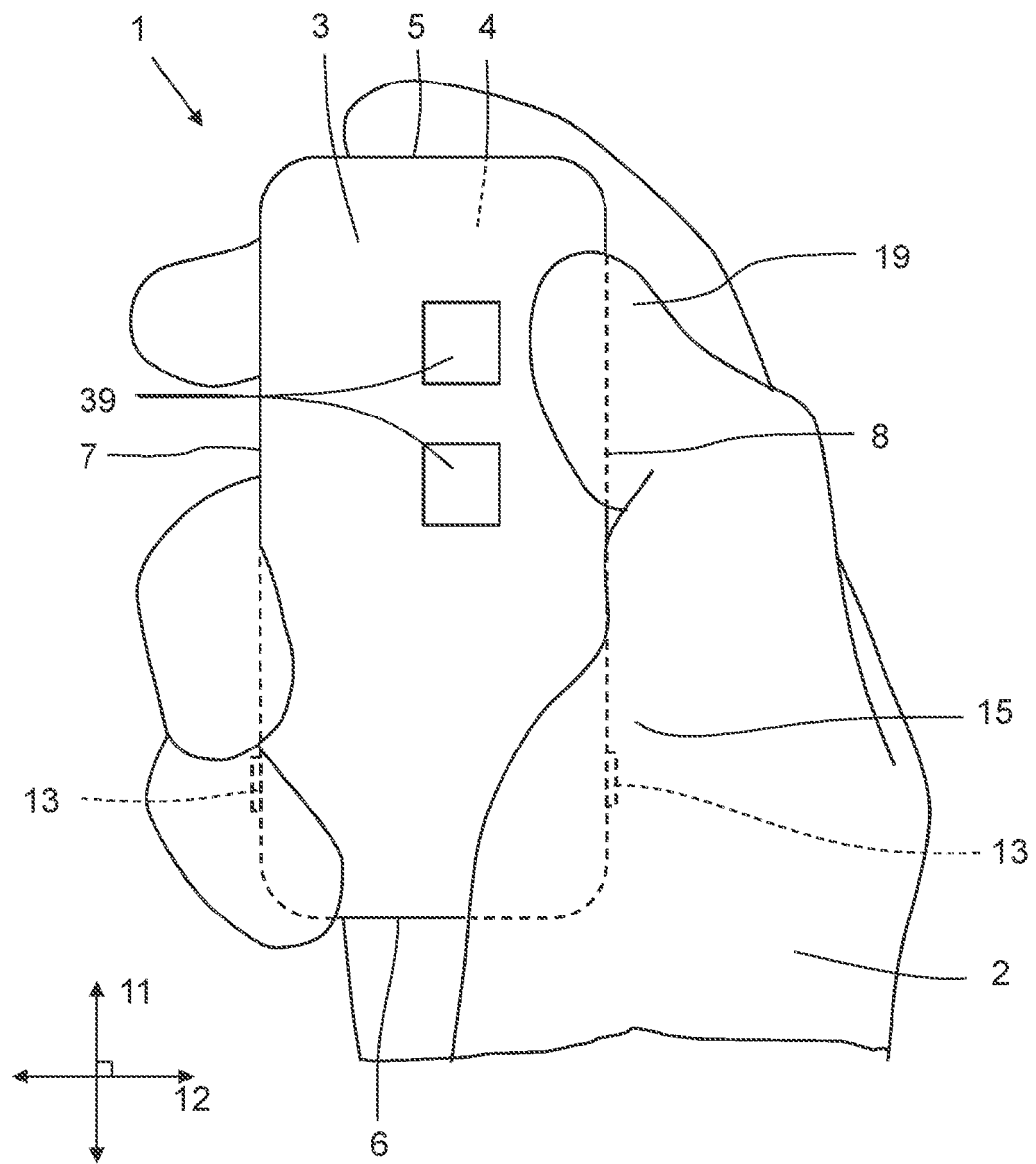
FIG. 10 shows a mobile device with side-looking sensors in form of a game controller.

As briefly mentioned above, the mobile device may be a mobile cellular telephone, as illustrated in any of FIGS. 1-7. However, the mobile device 1 may alternatively be, for example, handheld game controller 38 having one or more input devices 39, as illustrated in FIG. 10. One or mode side-looking sensors 13, such as, for example, on each of the left and right side surfaces 7, 8 as illustrated in FIG. 10, may be provided for detecting biometric data of user holding the controller 38, thereby enabling a more dynamic and interactive experience for the user. Still more alternatively, the mobile device may be a notebook computer, a tablet computer, a laptop computer or a portable media player.

The disclosure also relates to a method for sensing a biometric function of a user holding a mobile device 1 having a generally flat rectangular shape with a relatively large front and rear surfaces 3, 4 and relatively small upper side, lower side, left side and right side surfaces 5, 6, 7, 8. The method comprises the steps of emitting light from a light source 28 towards a hand 2 of the user and receiving by means of a photodetector 30 light emitted from the light source 28 and reflected back from the hand 2, wherein the sensor 13 is a side-looking sensor.

Although the disclosure has been described in relation to specific combinations of components, it should be readily appreciated that the components may be combined in other configurations as well which is clear for the skilled person when studying the present application. Thus, the above description of the example embodiments of the present disclosure and the accompanying drawings are to be regarded as a non-limiting example of the disclosure and the scope of protection is defined by the appended claims. Any reference sign in the claims should not be construed as limiting the scope.

The use of the word "a" or "an" in the specification may mean "one," but it is also consistent with the meaning of "one or more" or "at least one." The term "about" means, in general, the stated value plus or minus 10%, or more specifically plus or minus 5%. The use of the term "or" in the claims is used to mean "and/or" unless explicitly indicated to refer to alternatives only.

The terms "comprise", "comprises" "comprising", "have", "has", "having", "include", "includes", "including" are open-ended linking verbs. As a result, a method or device that "comprises," "has" or "includes," for example, one or more steps or elements, possesses those one or more steps or elements, but is not limited to possessing only those one or more elements.

What is claimed is:

1. A mobile device comprising:
   a generally flat rectangular shape with a relatively large front and rear surfaces and relatively small upper side, lower side, left side and right side surfaces, wherein the upper and lower side surfaces are smaller than the left and right side surfaces;
   at least one sensor located on the lower side surface, and configured for capturing first contact pressure data of a user holding the mobile device; and
   at least one sensor located on the upper side surface, and configured for capturing second contact pressure data of the user,
   wherein each sensor comprises:
      a light source configured for emitting light towards a hand of the user, and
      a photodetector configured for receiving light reflected from the hand that was emitted from the light source, and
   wherein each sensor is a side-looking sensor.

2. The mobile device according to claim 1, wherein at least one side-looking sensor on each of the left and right side surfaces is located in a lower third of the mobile device, as seen with the mobile device oriented in a vertical plane with the upper side surface facing upwards.

3. The mobile device according to claim 1, wherein the mobile device comprises at least two side-looking sensors configured for capturing biometric data on at least one of the side surfaces.

4. The mobile device according to claim 1, wherein at least one side-looking sensor on each of the left and right side surfaces is located in a lower third of the mobile device, and wherein at least one side-looking sensor on each of the left and right side surfaces is located in an upper third of the mobile device, as seen with the mobile device oriented in a vertical plane with the upper side surface facing upwards.

5. The mobile device according to claim 1, wherein the mobile device comprises at least one side-looking sensor configured for capturing biometric data on each side surface.

6. The mobile device according to claim 1, wherein the mobile device comprises at least two side-looking sensors configured for capturing biometric data on each side surface.

7. The mobile device according to claim 1, wherein the mobile device comprises at least two side-looking sensors configured for capturing biometric data on each of the left and right side surfaces, and wherein the mobile device comprises at least two side-looking sensors configured for capturing biometric data on each of the upper and lower side surfaces.

8. The mobile device according to claim 1, wherein the mobile device is a mobile cellular telephone, a notebook computer, a tablet computer, a laptop computer, a portable media player, a handheld game controller or a handheld game console.

9. The mobile device according to claim 1, wherein a facing direction of a photosensitive area of the photodetector is oriented perpendicular to a facing direction of the front surface.

10. A method for sensing a biometric function of a user holding a mobile device, wherein the mobile device comprises a generally flat rectangular shape with a relatively large front and rear surfaces and relatively small upper side, lower side, left side and right side surfaces, wherein the upper and lower side surfaces are smaller than the left and right side surfaces, wherein at least one sensor is located on the upper side surface and configured for capturing first contact pressure data, and at least one sensor is located on the lower side surface and configured for capturing second contact pressure data, wherein each sensor comprises a light source and a photodetector, and wherein each sensor is a side-looking sensor, the method comprising:

emitting first light from a first light source towards a first hand of the user;

emitting second light from a second light source towards a second hand of the user;

receiving by a first photodetector first reflected light from the first hand that was emitted from the first light source; and receiving by a second photodetector second reflected light from the second hand that was emitted from the second light source, wherein the first and second reflected light include the first and second contact pressure data.

11. The method according to claim 10, wherein the mobile device is a mobile cellular telephone, a notebook computer, a tablet computer, a laptop computer, a portable media player, a handheld game controller or a handheld game console.

12. The method according to claim 10, wherein facing directions of photosensitive areas of the first and second photodetectors are oriented perpendicular to a facing direction of the front surface.

* * * * *